(12) United States Patent
Takeuchi et al.

(10) Patent No.: US 11,896,043 B2
(45) Date of Patent: Feb. 13, 2024

(54) INTESTINAL IMMUNE-ENHANCING AGENT, FOOD PRODUCT, AND MEDICAMENT

(71) Applicant: DAICEL CORPORATION, Osaka (JP)

(72) Inventors: Tadashi Takeuchi, Wako (JP); Eiji Miyauchi, Wako (JP); Shu Shimamoto, Tokyo (JP); Akinobu Matsuyama, Tokyo (JP); Hiroshi Ohno, Wako (JP)

(73) Assignee: DAICEL CORPORATION, Osaka (JP)

( * ) Notice: Subject to any disclaimer, the term of this patent is extended or adjusted under 35 U.S.C. 154(b) by 175 days.

(21) Appl. No.: 17/476,131

(22) Filed: Sep. 15, 2021

(65) Prior Publication Data

US 2022/0061372 A1 Mar. 3, 2022

Related U.S. Application Data

(63) Continuation of application No. 16/759,074, filed as application No. PCT/JP2018/039373 on Oct. 23, 2018, now abandoned.

(30) Foreign Application Priority Data

Oct. 26, 2017 (JP) ................................ 2017-207154

(51) Int. Cl.
  *A23L 33/24* (2016.01)
  *A61K 31/717* (2006.01)
  *G06F 17/18* (2006.01)

(52) U.S. Cl.
  CPC ............ *A23L 33/24* (2016.08); *A61K 31/717* (2013.01); *G06F 17/18* (2013.01)

(58) Field of Classification Search
  CPC ........ A23L 33/24; A61K 31/717; G06F 17/18
  USPC ......................................................... 514/57
  See application file for complete search history.

(56) References Cited

U.S. PATENT DOCUMENTS

| 10,188,675 B2 | 1/2019 | Shimamoto et al. |
| 10,300,085 B2 | 5/2019 | Shimamoto et al. |
| 10,869,883 B2 | 12/2020 | Shimamoto et al. |
| 2002/0098112 A1 | 7/2002 | Hayashi |
| 2014/0220080 A1 | 8/2014 | Miyazato et al. |
| 2017/0100426 A1 | 4/2017 | Shimamoto et al. |

FOREIGN PATENT DOCUMENTS

| EP | 1 205 183 A2 | 5/2002 |
| JP | 2003-201239 A | 7/2003 |
| JP | 2014-152125 A | 8/2014 |
| JP | 2017-42054 A | 3/2017 |
| WO | WO 2015/093067 A1 | 6/2015 |
| WO | WO 2015/146853 A1 | 10/2015 |

OTHER PUBLICATIONS

Khor et al. Genetics and pathogenesis of inflammatory bowel disease. Nature vol. 474, pp. 307-317, 2011 (Year: 2011).*
Ubeda et al. Roles of the intestinal microbiota in pathogen protection. Clinical & Translational Immunology (2017) 6, e128; doi: 10.1038/cti.2017.2, published online Feb. 10, 2017 (Year: 2017).*
Extended European Search Report dated Jun. 21, 2021, in European Patent Application No. 18869730.4.
Hino et al., "Effect of Dietary Lactosucrose ( 4G-β-D-Galactosylsucrose) on the Intestinal Immune Functions in Mice", J. Appl. Glycosci, 2007, vol. 54, pp. 169-172.
Hosono, "Immunomodulation by *Bacteroides* species", 2013, vol. 27, ISSN 1343-0882, pp. 203-209.
International Search Report, issued in PCT/JP2018/039373, dated Jan. 8, 2019.
Office Action dated May 31, 2021, in Indian Patent Application No. 202047021248.
Sato et al., "Effects of Dietary Galactooligosaccharides on Immune System in Mice", J Jpn Soc Nutr Food Sci, 2008, vol. 61, pp. 79-88.
Scholtens et al., "Fecal secretory Immunoglobulin A is Increased in Healthy Infants Who Receive a Formula with Short-Chain Galacto-Oligosaccharides and Long-Chain Fructo-Oligosaccharides," J. Nutr. (2008), vol. 138, pp. 1141-1147.
Written Opininon of the International Searching Authority, issued in PCT/JP2018/039373, dated Jan. 8, 2019.
Korean Office Action for Korean Application No. 10-2020-7009822, dated Apr. 24, 2022, with English translation.

* cited by examiner

*Primary Examiner* — Yih-Horng Shiao

(74) *Attorney, Agent, or Firm* — Birch, Stewart, Kolasch & Birch, LLP

(57) ABSTRACT

Object of the present invention is to provide an intestinal immune-enhancing agent that can sufficiently increase IgA in the intestinal tract with a low dose while maintaining an increased amount of IgA for an extended period of time. Provided is an intestinal immune-enhancing agent containing a cellulose acetate that has a total degree of acetyl substitution from 0.4 to 1.1.

5 Claims, 5 Drawing Sheets

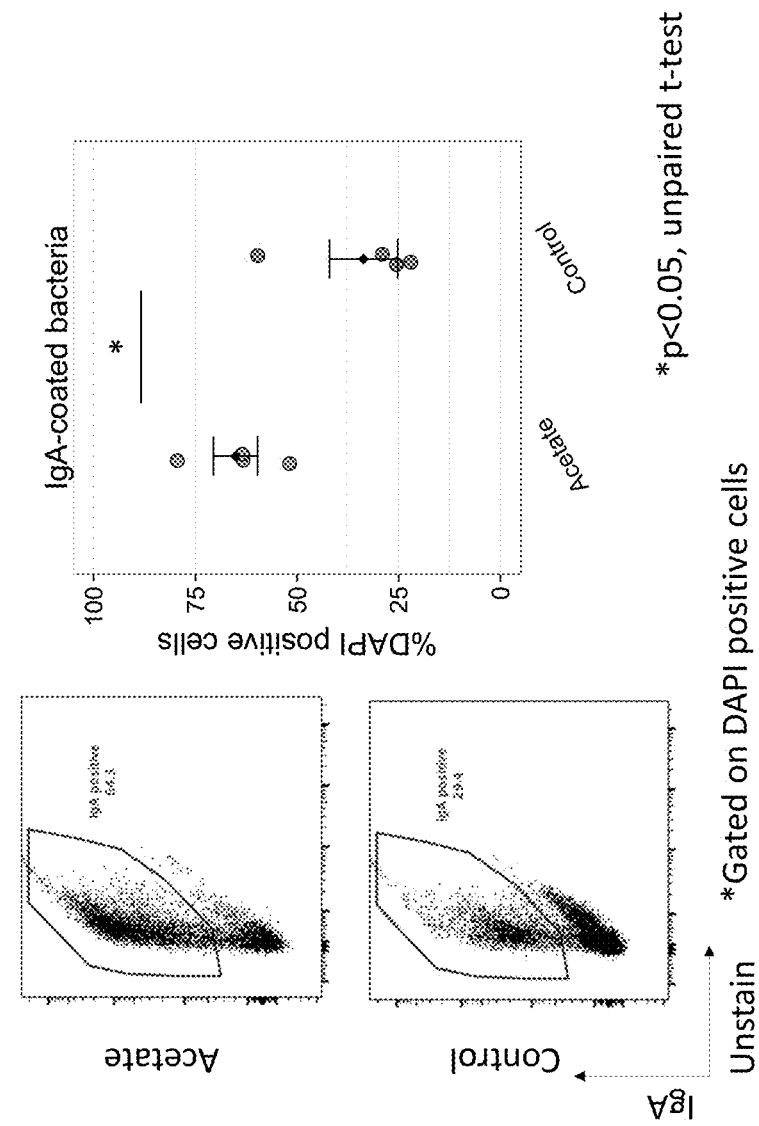

*: $p < 0.05$, : $p < 0.01$, *: $p < 0.001$, unpaired t-test.

INTESTINAL IMMUNE-ENHANCING AGENT, FOOD PRODUCT, AND MEDICAMENT

This application is a Continuation of co-pending application Ser. No. 16/759,074, filed on Apr. 24, 2020, which is the National Stage Application under 35 U.S.C. § 371 of International Application No. PCT/JP2018/039373, filed on Oct. 23, 2018, which claims the benefit under 35 U.S.C. § 119(a) to Japanese Patent Application No. 2017-207154, filed on Oct. 26, 2017, all of which are hereby expressly incorporated by reference into the present application.

TECHNICAL FIELD

The present invention relates to an intestinal immune-enhancing agent, a food product, and a medicament.

BACKGROUND ART

Immunoglobulins (Igs), a type of glycoprotein, have classes such as IgA, IgD, IgE, IgG, and IgM. Among these, IgA is present in mammals and avian species. In particular, IgA contained in exocrine fluids, such as saliva, tears, nasal discharge, airway mucus, gastrointestinal secretions, and breast milk is a secretory IgA that serves as the first line of defense of the immune mechanism in protecting the mucosal surface from antigens and microorganisms.

The gastrointestinal tract is always in contact with many substances, including antigens and microorganisms, and it is necessary to prevent these antigens and microorganisms from invading the body; specifically, IgA secreted by the intestinal tract is important to mucosal immune functions in preventing bacteria or viruses from adhering to mucosal surfaces and removing foreign substances by capturing foreign antigens and discharging them outside the body. Since promoting IgA secretion in the intestinal tract has promising effects such as enhancing mucosal immune functions and preventing infections or allergies, there is a demand for the development of food products and the like having IgA secretion promoting effect.

Non-Patent Literature 1 has the following description (Summary). "The effects of galactooligosaccharides, a type of indigestible oligosaccharide, on the murine immune system were examined. BALB/c mice were housed with free intake of feed containing galactooligosaccharides; 2 weeks after ingestion, the amount of total IgA contained in the feces increased significantly, and then returned to the same level as the control group. Four weeks later, the mice were sacrificed. The galactooligosaccharide group tended to have an increased total IgA of the prepared Peyer's patch cell culture and colon tissue extract."

Non-Patent Literature 2 contains description with the following information (Abstract). Lactosucrose ($4^G$-β-D-galactosylsucrose, LS) is suggested to be an oligosaccharide for the proliferation of Bifidobacteria in the intestine. Mice were fed with 2% and 5% LS added feed for 4 weeks, and the intestinal mucosal immune responses were determined. In the 2% and 5% LS fed groups, the amounts of IgA in the feces and cecal contents were significantly increased.

Patent Document 1 describes that fructooligosaccharides, a type of indigestible oligosaccharides, have been found to enhance IgA and pIgR production in the intestinal mucosa.

Patent Document 2 describes significant IgA secretion promoting effect by orally administering resistant dextrins.

Patent Document 3 describes a nutritional composition, livestock feed, lipid metabolism improving agent, inflammatory bowel disease and/or immune disorders prophylactic and/or therapeutic agent, cancer prophylactic and/or therapeutic agent, non-alcoholic steatohepatitis prophylactic and/or therapeutic agent, obesity and/or diabetes prophylactic and/or therapeutic agent, and hypercholesterolemia prophylactic and/or therapeutic agent containing a cellulose acetate that has a total degree of acetyl substitution from 0.4 to 1.1.

CITATION LIST

Patent Document

Patent Document 1: JP 2003-201239 A
Patent Document 2: JP 2014-152125 A
Patent Document 3: WO 2015/146853

Non-Patent Literature

Non-Patent Literature 1: Sato, et al. Effects of Dietary Galactooligosaccharides on Immune System in Mice. Journal of Japanese Society of Nutrition and Food Science. 2008, Vol. 61, No. 2, p. 79-88.
Non-Patent Literature 2: Hino Keiko, et al. Effect of Dietary Lactosucrose (4G-.BETA.-D-Galactosylsucrose) on the Intestinal Immune Functions in Mice. Journal of Applied Glycoscience. 2007, Vol. 54, No. 3, p. 169-172.

SUMMARY OF INVENTION

Technical Problem

Non-Patent Literature 1 describes that the ingestion of feed containing a galactooligosaccharide had the tendency to increase the total IgA in, for example, the colon tissue extracts of mice; however, the feed requires a dose containing as much as 5 wt. % of the galactooligosaccharide (the right column of p. 80, Table 2). In addition, during the second week of the ingestion of the feed containing a galactooligosaccharide, the total IgA in the feces of the test group that ingested the feed was up to about two times that of the control group and significant difference was observed; however, during the third week of the ingestion of the feed, the total IgA decreased to the same level as that of the control group and was not significantly different (the right column of p. 81, FIG. 1). Furthermore, after analysis of the colon tissue extracts and the like, it has been reported that the total IgA had the tendency to increase, but it has been stated that these effects do not have a significant difference (the right column of p. 81, FIGS. 2 and 3).

Non-Patent Literature 2 describes that while the amount of IgA in the feces of mice was about twice that of the control group one week after the ingestion of feed containing lactosucrose, the amount of IgA decreased greatly after two weeks, and then did not increase greatly (FIG. 1). Particularly, when fed with feed containing 2% of lactosucrose, the amount of IgA decreased greatly after 2 weeks, and then hardly increased (FIG. 1).

Patent Document 1 also describes that mice were fed with an experimental feed added with a fructooligosaccharide as much as 5% (w/w). While the IgA antibody content in the feces of 36-day-old mice of the test group fed with the experimental feed was approximately twice that of the control group and was significantly different (FIG. 5), no significant difference was observed from 28-day-old mice and 42-day-old mice in the same experiment (FIG. 5). In addition, while the total IgA antibody content in the colon of the test group among 44-day-old mice was approximately 1.5 times that of the control group (FIG. 7), the amount of IgA antibody per weight of colon tissue was not significantly different (FIG. 9). Furthermore, examination results (FIG. 14) of the amount of cholera toxin specific IgA against cholera bacteria, which belong to the phylum Proteobacteria, showed that the p-value between the test group and the control group was 0.07 which, given that the significance level was 5%, was not significantly different.

Patent Document 2 also describes that mice were fed with a control feed containing 5 mass % and 7.5 mass % of an indigestible dextrin. Although it has been shown that IgA in the gastrointestinal contents (FIG. 1) and feces (FIG. 2) has increased, the number of mice used in the experiment has not been shown, nor the results of significance test, and some figures did not even include error bars (FIGS. 1 to 4). Furthermore, it can be seen that the figures that include error bars have a large error range, and there was no description regarding the lack of significant difference as a result of the test. Thus, statistical verification has not been performed to determine whether the technique is one that increases IgA in the first place. Also, substrate specificity of IgA has not been examined.

Patent Document 3 describes a cellulose acetate that has a total degree of acetyl substitution from 0.4 to 1.1, but there is no mention or suggestion of an intestinal immune-enhancing agent.

Known methods of increasing IgA in the large intestine and the like using galactooligosaccharides, lactosucrose, fructooligosaccharides, indigestible dextrins, and the like requires a considerably high dose. If a high dose is required, it would be painful to take it orally as a pharmaceutical product when converted to the daily amount of human consumption, or, when ingested as a food product, the enjoyment of a normal meal would be compromised. Also, known methods cannot maintain an increased amount of IgA for an extended period of time. In addition, there is no design of IgA affinity for pathogenic bacteria (substrate specificity), and the specificity of IgA for pathogenic bacteria is low.

The object of the present invention is to provide an intestinal immune-enhancing agent that can sufficiently increase IgA in the intestinal tract with a low dose while maintaining an increased amount of IgA for an extended period of time.

Solution to Problem

A first aspect of the present invention relates to an intestinal immune-enhancing agent containing a cellulose acetate that has a total degree of acetyl substitution from 0.4 to 1.1.

The cellulose acetate of the intestinal immune-enhancing agent preferably has a compositional distribution index (CDI) of 2.0 or less, the compositional distribution index (CDI) being defined by the equation below.

CDI=(Measured value of half width of compositional distribution)/(Theoretical value of half width of compositional distribution)

Measured value of half width of compositional distribution: half width of compositional distribution determined by HPLC analysis of cellulose acetate propionate obtained by propionylation of all residual hydroxyl groups of cellulose acetate (sample).

Theoretical value of half width of compositional distribution=2.35482
$\sqrt{3 * DPw * (DS/3) * (1-DS/3)}/DPw$  [Equation 1]

DS: Total degree of acetyl substitution

DPw: Weight average degree of polymerization (value determined by GPC-light scattering using cellulose acetate propionate obtained by propionylation of all residual hydroxyl groups of cellulose acetate (sample))

A second aspect of the present invention relates to a food product containing the intestinal immune-enhancing agent. The content of the cellulose acetate in the food product is preferably 0.1 wt. % or more and less than 5 wt. %.

A third aspect of the present invention relates to a medicament containing the intestinal immune-enhancing agent.

Advantageous Effects of Invention

According to an embodiment of the present invention, an intestinal immune-enhancing agent that can sufficiently increase IgA in the intestinal tract with a low dose while maintaining an increased amount of IgA for an extended period of time can be provided.

BRIEF DESCRIPTION OF DRAWINGS

FIGS. 2A and 2B show the quantification results of IgA-coated bacteria in the feces of wild-type mice housed for four weeks. Specifically, FIG. 2A shows the primary data of flow cytometry, and FIG. 2B shows the percentage (%) of IgA-coated bacteria in DAPI positive cells (% DAPI positive cells).

FIG. 4A shows the primary data of flow cytometry, FIG. 4B shows the number of bacteria (absolute cell number) ($\times 10^4$).

FIG. 5A shows the percentage (%) of the number of IgA-coated bacteria in the DAPI positive cells (% DAPI positive cells) of the cecum (left: Cecal) and feces (right: Fecal) of *Bacteroides thetaiotaomicron* monocolonized mice. FIG. 5B shows the percentage (%) of the number of IgA-coated bacteria in the DAPI positive cells (% DAPI positive cells) of the cecum (left: Cecal) and feces (right: Fecal) of *E. coli* monocolonized mice, *E. coli* being a type of bacteria of the phylum Proteobacteria.

DESCRIPTION OF EMBODIMENTS

Intestinal Immune-Enhancing Agent

Figure 1:
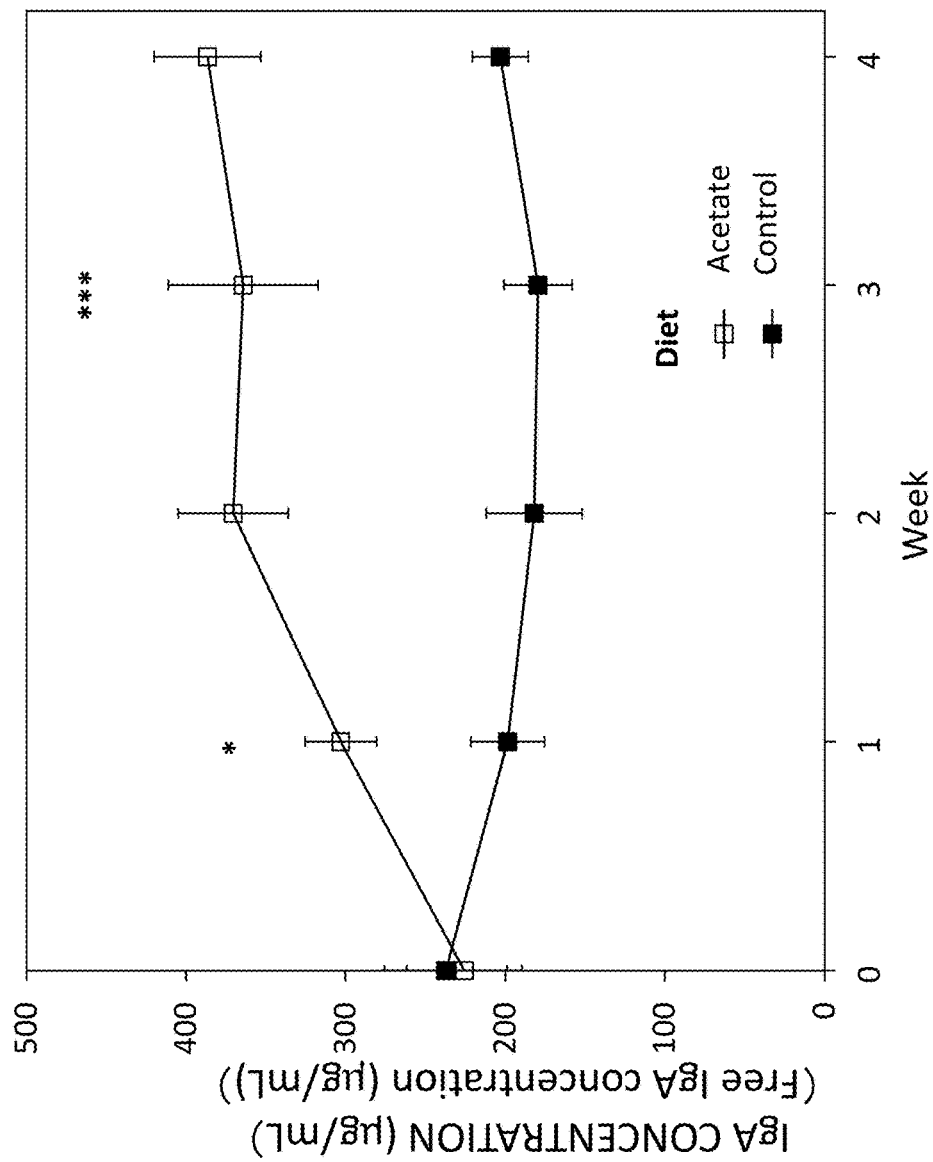
FIG. 1 shows the fecal IgA quantification results of wild-type mice.

The intestinal immune-enhancing agent according to an embodiment of the present disclosure contains a cellulose acetate that has a total degree of acetyl substitution from 0.4 to 1.1. Here, "intestinal tract" refers to the small intestine including duodenum, jejunum, ileum, and the like, as well as the large intestine including cecum, proximal colon, distal colon, and the like. Furthermore, "immune-enhancing" refers to, for example, increasing IgA, and the increase in IgA includes an increase in IgA-producing plasma cells.

Through the ingestion or administration (in particular, orally) of the intestinal immune-enhancing agent according to an embodiment of the present disclosure, the following effects can be achieved: immunoglobulin A (IgA)-producing plasma cells in the intestinal tract (especially the lamina propria of the large intestine) increases; IgA in the intestinal tract increases; the increased amount of IgA can be maintained for an extended period of time; and/or the increased antigen-antibody reaction specificity of IgA to bacteria in the phylum Proteobacteria reduces bacteria in the phylum Proteobacteria present in the intestinal mucosa. Proteobacteria is a phylum that includes many pathogenic bacteria such as pathogenic *E. coli*, *Salmonella*, *Vibrio* bacteria, and the reduction of these bacteria present in the mucosa of the large intestine protects the intestinal tract from pathogenic bacteria. Furthermore, the intestinal immune-enhancing agent according to an embodiment of the present disclosure is able to provide such effects even with a lower dose compared to known methods.

Total Degree of Acetyl Substitution of Cellulose Acetate

The cellulose acetate according to an embodiment of the present disclosure has a total degree of acetyl substitution (average degree of substitution) from 0.4 to 1.1. When a total degree of acetyl substitution is within this range, solubility in water of the cellulose acetate is excellent; however, when a total degree of acetyl substitution is outside this range, solubility in water of the cellulose acetate tends to decline. It is considered that cellulose acetate is broken down by intestinal bacteria into acetic acid and cellulose in the gastrointestinal tract, and the resulted cellulose is further broken down into short chain fatty acids such as acetic acid via oligosaccharides or monosaccharides. It is considered that metabolites such as acetic acid produced in such a process and intestinal bacteria that assimilate cellulose acetate in such a process lead to an increase in IgA-producing cells and in IgA. Because the breaking down of cellulose acetate into acetic acid and cellulose is thought to be caused by extracellular enzymes, cellulose acetate having a high solubility in water can be broken down more easily, and the effect of promoting an increase in IgA-producing cells and in IgA is high, further leading to greater efficacy of intestinal immunity enhancement. From such perspective, the range of the total degree of acetyl substitution is preferably from 0.5 to 1.0, and more preferably from 0.6 to 0.95.

The total degree of acetyl substitution can be measured by a known titration method, in which the degree of substitution of a cellulose acetate is determined after dissolving the cellulose acetate in water. Specifically, the measurement was performed as follows.

The total degree of acetyl substitution can be determined by determining a combined acetic acid to a method of measuring an acetyl content prescribed in ASTM D-817-91 (Standard Test Methods of Testing Cellulose Acetate relevant materials) and converting the resulted combined acetic acid into the total degree of acetyl substitution according to the equation below. This is the most common method of determining the degree of substitution of a cellulose acetate.

$$DS = 162.14 \times AV \times 0.01 / (60.052 - 42.037 \times AV \times 0.01)$$

DS: Total degree of acetyl substitution
AV: Combined acetic acid (%)

First, 500 mg of a dried cellulose acetate (sample) is precisely weighed and dissolved in 50 ml of a mixed solvent of ultrapure water and acetone (volume ratio of 4:1); then, 50 ml of a 0.2 N-sodium hydroxide solution is added, followed by saponification at 25° C. for 2 hours. Next, 50 ml of 0.2 N-hydrochloric acid is added, and the amount of acetic acid released is determined by titration with a 0.2 N-sodium hydroxide solution (0.2 N-sodium hydroxide normal solution) using Phenolphthalein as an indicator reagent. In addition, a blank test (test without using sample) is performed in the same manner. Then, the AV (degree of acetylation) (%) is calculated using the equation below.

$$AV\ (\%) = (A-B) \times F \times 1.201 / \text{sample weight (g)}$$

A: Titration amount of the 0.2 N-sodium hydroxide normal solution (ml)
B: Titration amount of the 0.2 N-sodium hydroxide normal solution (ml) in the blank test
F: Factor of the 0.2 N-sodium hydroxide normal solution In addition to the above, the total degree of acetyl substitution can also be measured by propionylation of hydroxyl groups of a cellulose acetate to obtain a cellulose acetate propionate, dissolving the cellulose acetate propionate in deuterated chloroform, and performing NMR analysis. The propionylation of hydroxyl groups of a cellulose acetate can be performed by a method of complete derivatization of a cellulose acetate described below, in which propionic anhydride is allowed to act upon the cellulose acetate by the catalysis of N,N-dimethylaminopyridine in a pyridine/N,N-dimethylacetamide mixed solvent.

Compositional Distribution Index (CDI) of Cellulose Acetate

In an embodiment according to the present disclosure, the compositional distribution index (CDI) of the cellulose acetate is not particularly limited. The compositional distribution index (CDI) may be, for example, from 1.0 to 3.0. The compositional distribution index (CDI) is preferably 2.0 or less, more preferably from 1.0 to 2.0, even more preferably from 1.0 to 1.8, even further more preferably from 1.0 to 1.6, and particularly preferably from 1.0 to 1.5.

The lower limit of the compositional distribution index (CDI) is 0, which can be achieved by special synthesis techniques such as a technique in which only six positions of a glucose residue are selectively acetylated with a selectivity of 100% while no other position is acetylated; however, such synthesis techniques have not yet been known. When all of the hydroxyl groups of the glucose residue are acetylated and deacetylated at the same probability, the CDI stands at 1.0; however, considerable efforts are required to approach the ideal state described above in actual cellulose reactions. The smaller the compositional distribution index (CDI), the more uniform the compositional distribution (intermolecular substitution degree distribution). Advantageously, the cellulose acetate, when having a uniform compositional distribution, can surely have a water solubility in a wider range of total degree of substitution as compared with conventional equivalents, can be uniformly dissolved, and does not develop a structural viscosity; thus, such cellulose acetate is easy to ingest or administer, breaks down easily, and express the effect of enhanced intestinal immunity easily.

Here, the "compositional distribution index" (CDI) is defined as the ratio of the measured value of half width of compositional distribution to the theoretical value of half width of compositional distribution [(Measured value of half width of compositional distribution)/(Theoretical value of half width of compositional distribution)]. The "half width of compositional distribution" is also referred to as "half width of intermolecular substitution degree distribution" or simply "half width of substitution degree distribution".

The evaluation of uniformity of the total degree of acetyl substitution of a cellulose acetate can be performed by using the magnitude of half width of a maximum peak (also referred to as "half-value width") in an intermolecular substitution degree distribution curve of the cellulose acetate as an index. Note that "half width" refers to the width of a chart at a height half the peak height (maximum height) in the chart, in which the chart is plotted with the horizontal axis (X-axis) indicating a degree of acetyl substitution and the vertical axis (Y-axis) indicating the abundance at that degree of acetyl substitution; the half width is an index indicating how the distribution disperses. The half width of substitution degree distribution can be determined by high-performance liquid chromatographic (HPLC) analysis. Note that a way to convert the horizontal axis (elution time) in an elution curve of a cellulose ester in HPLC into a degree of substitution (0 to 3) is described in JP 2003-201301 A (paragraphs 0037 to 0040).

Theoretical Value of Half Width of Compositional Distribution

The theoretical value of half width of compositional distribution (half width of substitution degree distribution) can be calculated stochastically. Specifically, the theoretical value of half width of compositional distribution can be determined according to Equation (1) below.

[Equation 2]

$$\text{Theoretical value of half width of compositional distribution} = 2.35482\sqrt{mpq}/DPw \quad (1)$$

m: Total number of hydroxy groups and acetyl groups per molecule of the cellulose acetate
p: Probability of substitution of hydroxy group with acetyl group per molecule of the cellulose acetate
q=1−p
DPw: Weight average degree of polymerization (as determined by the GPC-light scattering method)

Note that the method of measuring the weight average degree of polymerization (DPw) will be described below.

The theoretical value of half width of compositional distribution represented by Equation (1) is a half width of compositional distribution, which inevitably occurs when all hydroxy groups in a cellulose are acetylated and deacetylated at the same probability, and which is derived in accordance with the so-called binomial theorem. Furthermore, the theoretical value of half width of compositional distribution, when expressed by the degree of substitution and the degree of polymerization, is expressed as follows. Equation (2) below is defined as a definitional formula to determine the theoretical value of half width of compositional distribution.

[Equation 3]

$$\text{Theoretical value of half width of compositional distribution} = 2.35482\sqrt{3*DPw*(DS/3)*(1-DS/3)}/DPw \quad (2)$$

DS: Total degree of acetyl substitution
DPw: Weight average degree of polymerization (as determined by the GPC-light scattering method)

Note that the method of measuring the weight average degree of polymerization (DPw) will be described below.

In order to be more precise, Equations (1) and (2) should take the degree of polymerization distribution into consideration; in this case, "DPw" in Equations (1) and (2) should be replaced with the function of the degree of polymerization distribution, and the entire equations should be integrated from a degree of polymerization of 0 to infinity. However, Equations (1) and (2) give a theoretical value with an approximately sufficient precision, as long as they employ Dpw. When DPn (number average degree of polymerization) is employed in these equations, the influence of the degree of polymerization distribution becomes not negligible; thus, DPw should be used instead.

Measured Value of Half Width of Compositional Distribution

In an embodiment according to the present disclosure, the "measured value of half width of compositional distribution" refers to a half width of compositional distribution which is obtained by HPLC analysis using a cellulose acetate propionate obtained by propionylation of all residual hydroxy groups (unsubstituted hydroxy groups) of a cellulose acetate (sample).

In general, a cellulose acetate having a total degree of acetyl substitution of from 2 to 3 can be subjected to a high performance liquid chromatographic (HPLC) analysis without preprocessing, by which the half width of compositional distribution can be determined. For example, JP 2011-158664 A describes a method of analyzing the compositional distribution of a cellulose acetate having a degree of substitution from 2.27 to 2.56.

Meanwhile, the measured value of half width of compositional distribution (half width of substitution degree distribution) of the cellulose acetate according to an embodiment of the present disclosure is determined by subjecting residual hydroxy groups in the molecules of the cellulose acetate to derivatization as preprocessing before HPLC analysis, and then subjecting the derivative to the HPLC analysis. The preprocessing is performed in order to convert the cellulose acetate having a low degree of substitution (for example, a cellulose acetate having a total degree of acetyl substitution of 1.1 or less) into a derivative that can be easily dissolved in an organic solvent to enable the HPLC analysis. In other words, all residual hydroxy groups in the molecules are completely propionylated to give a completely derivatized cellulose acetate propionate (CAP), and the completely derivatized cellulose acetate propionate (CAP) is subject to HPLC analysis to determine the half width of compositional distribution (measured value). Here, the derivatization should be performed completely so that there are no residual hydroxyl groups in the molecules, and only acetyl and propionyl groups are present. That is, the sum of the total degree of acetyl substitution (DSac) and the total degree of propionyl substitution (DSpr) should be 3. This is because a relational expression, Dsac+Dspr=3, is used to plot a calibration curve so as to convert the horizontal axis (elution time) in the HPLC elution curve of the CAP into the total degree of acetyl substitution (from 0 to 3).

The complete derivatization of a cellulose acetate can be performed by allowing propionic anhydride to act upon the cellulose acetate by the catalysis of N,N-dimethylaminopyridine in a pyridine/N,N-dimethylacetamide mixed solvent. More specifically, the cellulose acetate is subjected to propionylation at a temperature of 100° C. for a reaction time of from 1.5 to 3.0 hours, using a mixed solvent [pyridine/N,N-dimethylacetamide=1/1 (v/v)] as the solvent in an amount of 20 parts by weight relative to the cellulose acetate (sample), using propionic anhydride as the propionylation of agent in an amount from 6.0 to 7.5 equivalents relative to hydroxy groups of the cellulose acetate, using N,N-dimethylaminopyridine as the catalyst in an amount from 6.5 to 8.0 mol % relative to the hydroxy groups of the cellulose acetate. The reaction mixture after the reaction is subjected to precipitation using methanol as the precipitation solvent and yields a completely derivatized cellulose acetate propionate. More specifically, for example, 1 part by weight of the reaction mixture is placed into 10 parts by weight of methanol at room temperature to give precipitates; then, the precipitates are washed with methanol five times, vacuum-dried at 60° C. for 3 hours, and yields a completely derivatized cellulose acetate propionate (CAP). Note that the dispersity (polydispersity, Mw/Mn) and weight average degree of polymerization (DPw) described below are determined by derivatizing the cellulose acetate (sample) by this method to give a completely derivatized cellulose acetate propionate (CAP), and measuring the parameters using the completely derivatized cellulose acetate propionate (CAP).

The HPLC analysis described above can be performed in the following manner. A plurality of cellulose acetate propionates having different degrees of total acetyl substitution as reference samples are subjected to HPLC analysis using a predetermined measuring apparatus under predetermined measuring conditions, and values of these reference samples measured by the analysis are plotted to give a calibration curve [the calibration curve indicates a relationship between the elution time and the total degree of acetyl substitution (from 0 to 3) of the cellulose acetate propionates and is generally a cubic curve]. On the basis of the calibration curve, the half width of compositional distribution (measured value) of the cellulose acetate (sample) can be determined. The HPLC analysis determines the relationship between the elution time and the total degree of acetyl substitution distribution of cellulose acetate propionates. This is the relationship between the elution time and the total degree of acetyl substitution distribution of a substance in which all remaining hydroxy groups in the sample molecules have been converted into propionyloxy groups; therefore, this determination is essentially not different from the determination of the total degree of acetyl substitution distribution of the cellulose acetate according to an embodiment in the present disclosure.

The HPLC analysis described above is performed under the following conditions.
  Device: Agilent 1100 Series
  Columns: Waters Nova-Pak phenyl 60 Å 4 μm (150 mm×3.9 mmΦ)+guard column
  Column temperature: 30° C.
  Detector: Varian 380-LC
  Injection volume: 5.0 μL (sample concentration: 0.1% (wt/vol))
  Eluents: Eluent A: MeOH/$H_2O$=8/1 (v/v), Eluent B: $CHCl_3$/MeOH=8/1 (v/v)
  Gradient: A/B=80/20→0/100 (28 min); Flow rate: 0.7 mL/min A substitution degree distribution curve (also referred to as an "intermolecular substitution degree distribution curve") is determined from the calibration curve [the substitution degree distribution curve is one of the cellulose acetate propionate, with the vertical axis indicating the abundance of the cellulose acetate propionate and the horizontal axis indicating the total degree of acetyl substitution]. On the substitution degree distribution curve, a half width of substitution degree distribution is determined by the maximum peak (E) corresponding to the average degree of substitution in the following manner. A base line (A-B) is drawn between a base point (A) at a lower degree of substitution and a base point (B) at a higher degree of substitution of the maximum peak (E) and is tangent to the base point (A) and the base point (B). With respect to the base line, a perpendicular line is drawn from the maximum peak (E) toward the horizontal axis. An intersection (C) of the perpendicular line and the base line (A-B) is determined. A midpoint (D) between the maximum peak (E) and the intersection (C) is then determined. A line including the midpoint (D) is drawn parallel to the base line (A-B) to determine two intersections (A' and B') of the line and the intermolecular substitution degree distribution curve. From the two intersections (A' and B'), lines perpendicular to the horizontal axis are drawn. The interval between the two X-intercepts of the thus-drawn perpendicular lines is defined as the half width of the maximum peak (namely, the half width of substitution degree distribution).

The half width of substitution degree distribution described above reflects that the retention times of cellulose acetate propionate molecule chains contained in the sample vary depending on how much the hydroxyl groups of glucose rings in individual polymer chains constituting the cellulose acetate propionate molecule chains are acetylated. Therefore, the width of the retention time ideally indicates the width of compositional distribution (in the substitution degree unit). However, HPLC analysis includes a duct that does not contribute to the distribution (such as a guide column for protecting the measuring column). Therefore, the width of retention time often includes an error that is caused not by the width of compositional distribution, but by the configuration of the measuring apparatus. The error is affected typically by the length and inner diameter of the column and by the length and routing of piping from the column to the detector, and varies depending on the configuration of the measuring apparatus, as mentioned above. Thus, the half width of substitution degree distribution of the cellulose acetate propionate can be determined as a correction value Z corrected according to a correction formula below. The correction formula can give a more accurate half width of substitution degree distribution as the same (or approximately the same) value not depending on the type of the measuring apparatus and the measuring conditions.

$$Z=(X^2-Y^2)^{1/2}$$

where X represents the half width of substitution degree distribution (uncorrected value) determined with the predetermined measuring apparatus under predetermined measuring conditions; Y=(a−b)x/3+b(0≤x≤3); "a" represents the apparent half width of substitution degree distribution of a cellulose acetate having a total degree of substitution of 3 as determined with the same measuring apparatus under the same measuring conditions as in X described above (this cellulose acetate does not actually have a substitution degree distribution because the total degree of substitution is 3); "b" represents the apparent height width of substitution degree distribution of a cellulose propionate having a total degree of substitution of 3 as determined with the same measuring apparatus under the same measuring conditions as in X described above; and "x" represents the total degree of acetyl substitution of the measurement sample (0≤x≤3).

Note that the "cellulose acetate (or cellulose propionate) having a total degree of substitution of 3" refers to a cellulose ester in which all hydroxyl groups of the cellulose are esterified, and actually (ideally) does not have a half width of substitution degree distribution (namely, ideally has a half width of substitution degree distribution of 0).

The measured value of the half width of compositional distribution (half width of substitution degree distribution) of the cellulose acetate is preferably from 0.12 to 0.34, more preferably from 0.13 to 0.31, and even more preferably from 0.13 to 0.25.

The theoretical formula of substitution degree distribution described above gives a stochastically calculated value on the assumption that all acetylation and deacetylation proceed independently and evenly; that is, the formula gives a calculated value according to a binomial distribution. Realistically, however, such ideal situation is unlikely to occur. A cellulose ester has a substitution degree distribution significantly wider than one stochastically determined according to the binomial distribution, unless an special approach is made to allow the hydrolysis reaction of the cellulose acetate to approach the ideal random reaction and/or is made to perform post-processing after the reaction so as to give fractionation in the composition.

One possible special approach to the reaction is exemplified by maintaining the system under conditions where deacetylation and acetylation are in equilibrium. However, in this case, decomposition of the cellulose progresses due to an acid catalyst, hence this plan is not preferable. Another example of special approaches to the reaction is the employment of reaction conditions where deacetylation proceeds at a lower rate for a low-substituted cellulose ester. However, no specific method to achieve this has yet been known. That is, there is no known special approach to the reaction to control the substitution degree distribution of a cellulose ester so as to be in accordance with the binomial distribution reaction stochastically. In addition, there are various circumstances, such as ununiformity of the acetylation process (the cellulose acetylation step) and partial/temporal precipitation caused by water added stepwise in the ripening process (the cellulose acetate hydrolysis process). These circumstances cause the substitution degree distribution to be wider than the binomial distribution. The reality is that it is impossible to avoid all of the circumstances and to achieve the ideal conditions. This resembles that an ideal gas is only a product of ideals, and an actual gas behaves somewhat differently from the ideal gas.

Known techniques relating to the synthesis and post-processing of a cellulose acetate having a low degree of substitution have paid little attention to the issues of the substitution degree distribution and have not performed measurement, verification, and examination of the substitution degree distribution. For example, according to the literature (Journal of the Society of Fiber Science and Technology, Japan, 42, p. 25 (1986)), the solubility of a cellulose acetate having a low degree of substitution is determined by the distribution of acetyl groups to the 2-, 3-, and 6-positions of glucose residue, and no consideration is given to the compositional distribution at all.

However, the present inventors made investigations and have found that, surprisingly, the substitution degree distribution of a cellulose acetate can be controlled by adjusting the conditions of the post-processing after the cellulose acetate hydrolysis step, as described later. According to other literature (CiBment, L., and Rivibre, C., Bull. SOC. chim., (5) 1, 1075 (1934); Sookne, A. M., Rutherford, H. A., Mark, H., and Harris, M. J. Research Natl. Bur. Standards, 29, 123 (1942); A. J. Rosenthal, B. B. White Ind. Eng. Chem., 1952, 44 (11), pp 2693-2696), a cellulose acetate having a total degree of substitution of 2.3 offers, upon precipitation fractionation, a fractionation depending on the molecular weight and a trivial fractionation accompanied with the degree of substitution (chemical composition). It has not yet been reported that the degree of substitution (chemical composition) as has been found by the present inventors can cause a significant fractionation. In addition, it has not yet been verified that the substitution degree distribution (chemical composition) of a cellulose acetate having a low degree of substitution can be controlled by dissolution fractionation or precipitation fractionation.

Another approach found by the present inventors to narrow the substitution degree distribution is a hydrolysis reaction (ripening reaction) of the cellulose acetate performed at a high temperature of 90° C. or above (or higher than 90° C.). The known techniques fail to make detailed analyses and considerations on the degree of polymerization of a product obtained by a high-temperature reaction, but people have believed that cellulose decomposition preferentially occurs in a high-temperature reaction at 90° C. or higher. This view is considered to be an assumption (stereotype) based only on considerations on viscosity. The present inventors have found as follows. Assuming that, upon hydrolysis to give a cellulose acetate having a low degree of substitution, the reaction of a cellulose acetate is performed in a large amount of acetic acid at a high temperature of 90° C. or above (or higher than 90° C.), preferably in the presence of a strong acid such as sulfuric acid. In this case, while the degree of polymerization of the cellulose acetate does not decrease, the viscosity decreases with decreasing CDI. That is, the present inventors have clarified that the decrease in viscosity with the high-temperature reaction is caused not by decrease in degree of polymerization, but by decrease in structural viscosity because of narrowed substitution degree distribution. When the cellulose acetate is hydrolyzed under the above conditions, the product (cellulose acetate having a low degree of substitution) has an extremely low CDI and significantly better solubility in water. This is because not only a forward reaction, but also a reverse reaction occurs upon the hydrolysis. In contrast to this, when the cellulose acetate is hydrolyzed under conditions where reverse reaction is unlikely to occur, the resulting product has a wider substitution degree distribution due to various factors and includes larger contents of cellulose acetates having a total degree of acetyl substitution of less than 0.4 and cellulose acetates having a total degree of acetyl substitution of greater than 1.1, both of which are poorly soluble in water. Thus, the resulting product as a whole has lower solubility in water.

Standard Deviation of Degree of Substitution at 2-, 3-, and 6-Positions

The total degrees of acetyl substitution at the 2-, 3-, and 6-positions of the glucose ring of the cellulose acetate can be measured by the NMR method described by Tezuka (Tezuka, Carbonydr. Res. 273, 83 (1995)). That is, free hydroxy groups of a cellulose acetate sample are propionylated with propionic anhydride in pyridine. The resulting sample is dissolved in deuterated chloroform and subjected to $^{13}$C-NMR spectrum measurement. Carbon signals of the acetyl groups appear in the order of the 2-position, 3-position, and 6-position from a higher magnetic field in a region of from 169 ppm to 171 ppm, and carbonyl carbon signals of the propionyl groups appear in the same order in a region of from 172 ppm to 174 ppm. The degrees of acetyl substitution at the 2-, 3-, and 6-positions of the glucose ring of the original cellulose acetate can be determined on the basis of the abundance ratio of acetyl groups and propionyl groups at their corresponding positions. Note that the sum of the thus-obtained degrees of acetyl substitution at the 2-, 3-, and 6-positions is the "total degree of acetyl substitution", and the total degree of acetyl substitution can also be determined in the above manner. Note that the total degree of acetyl substitution can be analyzed not only by $^{13}$C-NMR but also by $^1$H-NMR.

The standard deviation 6 of the degrees of substitution at the 2-, 3-, and 6-positions is defined by the equation below.

$$\sigma^2 = \frac{1}{n-1}\sum_{i=1}^{n}(x_i - \bar{x})^2 \qquad \text{[Equation 4]}$$

σ=Standard deviation
n=3
$x_i$=$x_1$ represents the degree of substitution at the 2-position, $x_2$ represents the degree of substitution a the 3-position, and $x_3$ represents the degree of substitution at the 6-position
x̃: Total degree of acetyl substitution/3

The cellulose acetate preferably has a standard deviation of degrees of acetyl substitution at the 2-, 3-, and 6-positions of the glucose ring of 0.08 or less (from 0 to 0.08). The cellulose acetate, when having a standard deviation of 0.08 or less, is approximately evenly substituted at the 2-, 3-, and 6-positions of the glucose ring and is highly soluble in water.

Dispersity (Polydispersity, Mw/Mn)

The dispersity (polydispersity, Mw/Mn) of the molecular weight distribution (polymerization degree distribution) refers to a value determined by the GPC-light scattering method using a cellulose acetate propionate obtained by propionylation of all residual hydroxy groups of the cellulose acetate (sample).

The cellulose acetate according to an embodiment of the present disclosure preferably has a dispersity (polydispersity, Mw/Mn) of from 1.2 to 2.5. The cellulose acetate, when having a dispersity Mw/Mn within the range described above, includes molecules of approximately uniform sizes and is highly soluble in water. It is considered that cellulose acetate is broken down by intestinal bacteria into acetic acid and cellulose in the gastrointestinal tract, and the resulted cellulose is further broken down into short chain fatty acids such as acetic acid via oligosaccharides or monosaccharides. It is considered that metabolites such as acetic acid produced in such a process and intestinal bacteria that assimilate cellulose acetate in such a process lead to an increase in IgA-producing cells and in IgA. Because the breaking down of cellulose acetate into acetic acid and cellulose is thought to be caused by extracellular enzymes, cellulose acetate having a high solubility in water can be broken down more easily, and the effect of promoting an increase in IgA-producing cells and in IgA is high, further leading to greater efficacy of intestinal immunity enhancement.

The number average molecular weight (Mn), weight average molecular weight (Mw), and dispersity (polydispersity, Mw/Mn) of the cellulose acetate can be determined by known methods using HPLC. The dispersity (polydispersity, Mw/Mn) of the cellulose acetate can be determined in the following manner. The cellulose acetate (sample) is converted into a completely derivatized cellulose acetate propionate (CAP) by a procedure similar to that in the determination of the measured value of half width of compositional distribution, so as to render a measurement sample soluble in an organic solvent. The completely derivatized cellulose acetate propionate is then analyzed by size exclusion chromatography under the following conditions (GPC-light scattering method).

Apparatus: GPC "SYSTEM-21 H", available from Shodex
Solvent: Acetone
Column: Two GMHxl columns (available from Tosoh Corporation) with guard columns (TSKgel guardcolumn HXL-H, available from Tosoh Corporation)
Flow rate: 0.8 ml/min
Temperature: 29° C.
Sample concentration: 0.25% (wt/vol)
Injection volume: 100 μl
Detector: MALLS (multi-angle light scattering detector) ("DAWN-EOS", available from Wyatt)
Reference material for MALLS correction: PMMA (having a molecular weight of 27600)

Weight Average Degree of Polymerization (DPw)

The "weight average degree of polymerization (DPw)" refers to a value determined by the GPC-light scattering method using a cellulose acetate propionate obtained by propionylation of all residual hydroxy groups of the cellulose acetate (sample).

The cellulose acetate according to an embodiment of the present disclosure preferably has a weight average degree of polymerization (DPw) of from 50 to 800. The cellulose acetate, when having an excessively high weight average degree of polymerization (DPw), tends to have poor solubility in water. The weight average degree of polymerization (DPw) of the cellulose acetate is preferably from 55 to 700, and more preferably from 60 to 600. It is considered that cellulose acetate is broken down by intestinal bacteria into acetic acid and cellulose in the gastrointestinal tract, and the resulted cellulose is further broken down into short chain fatty acids such as acetic acid via oligosaccharides or monosaccharides. It is considered that metabolites such as acetic acid produced in such a process and intestinal bacteria that assimilate cellulose acetate in such a process lead to an increase in IgA-producing cells and in IgA. Because the breaking down of cellulose acetate into acetic acid and cellulose is thought to be caused by extracellular enzymes, cellulose acetate having a high solubility in water can be broken down more easily, and the effect of promoting an increase in IgA-producing cells and in IgA is high, further leading to greater efficacy of intestinal immunity enhancement.

The weight average degree of polymerization (DPw) can be determined in the following manner. The cellulose acetate (sample) is converted into a completely derivatized cellulose acetate propionate (CAP) by a procedure similar to that in the determination of the measured value of half width of compositional distribution. The completely derivatized cellulose acetate propionate is then analyzed by size exclusion chromatography to determine the weight average degree of polymerization (DPw) (GPC-light scattering method), as in the determination of the dispersity (polydispersity, Mw/Mn).

As described above, the molecular weight (degree of polymerization) and dispersity (polydispersity, Mw/Mn) of a cellulose acetate are measured by the GPC-light scattering method (for example, GPC-MALLS or GPC-LALLS). Note that, light scattering detection is generally difficult in an aqueous solvent. This is because an aqueous solvent typically includes a large amount of foreign substances and is prone to secondary contamination even when purified. In addition, the aqueous solvent may have unstable spreading of its molecular chain due to ionic dissociation groups present in trace amounts; when a water-soluble inorganic salt (for example, sodium chloride) is added to suppress this, the dissolved state may become unstable, and an aggregate may be formed in the resulting aqueous solution. In one of effective methods to avoid this issue, the cellulose acetate is derivatized so as to be soluble in an organic solvent, and subjected to GPC-light scattering measurement in the organic solvent, because such an organic solvent contains a small amount of foreign substances and is resistant to secondary contamination. The derivatization of the cellulose acetate for this purpose effectively employs propionylation. Specific reaction conditions and post-processing are as described in the determination of the measured value of half width of compositional distribution.

Production of Cellulose Acetate

The cellulose acetate (cellulose acetate) may be produced, for example, by a hydrolysis step (ripening step) (A), a precipitation step (B), and a washing/neutralizing step (C); in the hydrolysis step (A), a cellulose acetate having a medium to high degree of substitution is hydrolyzed; the washing/neutralizing step (C) may be performed as needed. Note that the total degree of acetyl substitution of cellulose acetate having a medium to high degree of substitution is, for example, from 1.5 to 3, and preferably from 2 to 3.

(A) Hydrolysis Step (Ripening Step)

The hydrolysis reaction may be performed by allowing the raw material cellulose acetate to react with water in an organic solvent in the presence of a catalyst (ripening catalyst). Examples of the organic solvent include acetic acid, acetone, alcohols (such as methanol), and mixed solvents thereof. Among these, a solvent containing at least acetic acid is preferred. A catalyst commonly used as a deacetylation catalyst can be used as the catalyst. Sulfuric acid is particularly preferable as the catalyst.

The amount of the organic solvent (for example, acetic acid) used is, for example, from 0.5 to 50 parts by weight, preferably from 1 to 20 parts by weight, and more preferably from 3 to 10 parts by weight, based on 1 part by weight of the raw material cellulose acetate.

The amount of the catalyst (for example, sulfuric acid) used is, for example, from 0.005 to 1 parts by weight, preferably from 0.01 to 0.5 parts by weight, and more preferably from 0.02 to 0.3 parts by weight, based on 1 part by weight of the raw material cellulose acetate. The catalyst, when used in an excessively small amount, may cause the hydrolysis to require an excessively long time and may thereby cause the target cellulose acetate to have a lower molecular weight. In contrast, the catalyst, when used in an excessively large amount, may cause a larger variation of the depolymerization rate depending on the hydrolysis temperature, thereby causing a high depolymerization rate even at a relatively low hydrolysis temperature, which may impede the production of a cellulose acetate having a certain high level of molecular weight.

The amount of water used in the hydrolysis step is, for example, from 0.5 to 20 parts by weight, preferably from 1 to 10 parts by weight, and more preferably from 2 to 7 parts by weight, based on 1 part by weight of the raw material cellulose acetate. In addition, the amount of water used is, for example, from 0.1 to 5 parts by weight, preferably from 0.3 to 2 parts by weight, and more preferably from 0.5 to 1.5 parts by weight, based on 1 part by weight of the organic solvent (for example, acetic acid). The water may be present in the whole quantity in the system at the start of the reaction; however, to prevent precipitation of cellulose acetate, a portion of the water to be used may be present in the system at the start of the reaction, with the remaining water being added to the system in one or several batches during the reaction.

The reaction temperature in the hydrolysis step is, for example, from 40 to 130° C., preferably from 50 to 120° C., more preferably from 60 to 110° C. In particular, the reaction may be performed at a temperature of 90° C. or above (or at a temperature higher than 90° C.). In this case, the reaction equilibrium tends to be such that the rate of a reverse reaction (acetylation reaction) relative to a forward reaction (hydrolysis reaction) increases. This narrows the substitution degree distribution and can result in a cellulose acetate having a very low compositional distribution index CDI without specially adjusting the post-processing conditions. In this case, it is preferable to use a strong acid such as sulfuric acid as the catalyst, and it is preferable to use an excess amount of acetic acid as the reaction solvent. In addition, even when the reaction is performed at a temperature of 90° C. or lower, a cellulose acetate having a very low compositional distribution index CDI can be obtained by performing precipitation using a mixed solvent including two or more different solvents as a precipitation solvent in the precipitation step, and by performing precipitation fractionation and/or dissolution fractionation in the precipitation step, as described below.

(B) Precipitation Step

In this step, after the completion of the hydrolysis reaction, the temperature of the reaction system is cooled to room temperature, and the precipitation solvent is added to precipitate the cellulose acetate. An organic solvent miscible with water or an organic solvent having high solubility in water can be used as the precipitation solvent. Examples of such solvents include ketones such as acetone and methyl ethyl ketone; alcohols such as methanol, ethanol, isopropyl alcohol; esters such as ethyl acetate; nitrogen-containing compounds such as acetonitrile; ethers such as tetrahydrofuran; and mixed solvents thereof.

When a mixed solvent including two or more solvents is used as the precipitation solvent, the same effects as the precipitation fractionation described below can be obtained, and a cellulose acetate having a narrow compositional distribution (intermolecular substitution degree distribution) and a low compositional distribution index CDI can be obtained. Preferable mixed solvents include, for example, a mixed solvent of acetone and methanol, and a mixed solvent of isopropyl alcohol and methanol.

Furthermore, by performing precipitation fractionation (fractional precipitation) and/or dissolution fractionation (fractional dissolution) on the cellulose acetate obtained by precipitation, a cellulose acetate having a narrow compositional distribution (intermolecular substitution degree distribution) and a very low compositional distribution index CDI can be obtained.

The precipitation fractionation may be performed typically in the following manner. The cellulose acetate (solid) obtained by precipitation is dissolved in water to give an aqueous solution having an appropriate concentration (typically from 2 to 10 wt. %, and preferably from 3 to 8 wt. %). A poor solvent is added to the aqueous solution (or, the aqueous solution is added to the poor solvent), and the mixture is held at an appropriate temperature (typically 30° C. or lower, and preferably 20° C. or lower) to precipitate a cellulose acetate, and the precipitate is collected. Examples of the poor solvent include alcohols such as methanol, and ketones such as acetone. The poor solvent may be used in an amount, for example, from 1 to 10 parts by weight, and preferably from 2 to 7 parts by weight, per 1 part by weight of the aqueous solution.

The dissolution fractionation may be performed typically in the following manner. The cellulose acetate (solid) obtained by precipitation or the cellulose acetate (solid) obtained by precipitation fractionation is combined with a mixed solvent of water and an organic solvent (for example, ketones such as acetone, alcohols such as ethanol). The mixture is stirred at an appropriate temperature (for example, from 20° C. to 80° C., and preferably from to 60° C.) and separated into a dense phase and a dilute phase by centrifugation. The dilute phase is combined with a precipitation solvent (for example, ketones such as acetone, alcohols such as methanol), and the precipitate (solid) is collected. The concentration of the organic solvent in the mixed solvent of the water and the organic solvent is, for example, from 5 to 50 wt. %, and preferably from 10 to 40 wt. %.

(C) Washing/Neutralizing Step

The precipitate (solid) obtained from the precipitation step (B) is preferably washed with an organic solvent (poor solvent); examples of the organic solvent (poor solvent) include alcohols such as methanol or ketones such as acetone. It is also preferable to wash and neutralize the precipitate with an organic solvent containing a basic substance (for example, alcohols such as methanol, ketones such as acetone). Note that the neutralizing step may be performed immediately after the hydrolysis step; in this case, it is preferable to add the basic substance or an aqueous solution of the basic substance to the hydrolysis reaction bath.

Examples of the basic substance include alkali metal compounds and alkaline earth metal compounds. Specific examples of the alkali metal compounds include: alkali metal hydroxides such as sodium hydroxide and potassium hydroxide; alkali metal carbonates such as sodium carbonate and potassium carbonate; alkali metal hydrogen carbonates such as sodium hydrogen carbonate; alkali metal carboxylates such as sodium acetate and potassium acetate; and sodium alkoxides such as sodium methoxide and sodium ethoxide. Specific examples of the alkaline earth metal compounds include: alkaline earth metal hydroxides such as magnesium hydroxide and calcium hydroxide; alkaline earth metal carbonates such as magnesium carbonate and calcium carbonate; alkaline earth metal carboxylates such as magnesium acetate and calcium acetate; and alkaline earth metal alkoxides such as magnesium ethoxide. Among these, alkali metal compounds such as potassium acetate are preferred.

By washing and neutralization, impurities such as the catalyst (such as sulfuric acid) used in the hydrolysis step can be efficiently removed.

The cellulose acetate obtained in the above manner can be pulverized, sorted, or granulated as needed to have a particle size within a certain range.

Food Product, Medicament

The intestinal immune-enhancing agent according to an embodiment of the present disclosure can be contained in a food product or a medicament; as described below, while a cellulose acetate having an total degree of acetyl substitution from 0.4 to 1.1 alone may be used as a food or a medicament, such cellulose acetate can be used as a component of various food products or medicaments.

Examples of a method of ingesting or administering the food product or medicament includes, in particular, oral ingestion or administration. Various forms can be selected. For example, common pharmaceutical forms such as powders, granules, tablets, sugar-coated tablets, capsules, syrups, pills, suspensions, solutions, and emulsions, as well as common food product forms such as beverages; confectionery products such as gum, chocolate, candy, yokan (adzuki-bean jelly), and jelly; noodles; baked products such as bread, cakes, biscuits; canned food products; retort food products; livestock meat food products; fish paste products; edible oil compositions such as margarine, dressings, and mayonnaise; dietary supplements; milk products such as butter, ice cream, yogurt.

The food product or medicament according to an embodiment of the present disclosure can be applied not only to humans but also to animals such as domestic animals (bovine, porcine, equine, ovine, etc.), poultry (chickens, ducks, etc.), pets (dogs, cats, monkeys, mice, rats, guinea pigs, etc.). Among these, as a dose for obtaining an effect in humans, intake from 1 g to 10 g per day is preferable for cellulose acetate; sugar-coated tablets, noodles, and baked products such as biscuits are preferred since a relatively large amount can be ingested. The intestinal immune-enhancing agent according to an embodiment of the present disclosure can also be incorporated as a thickening agent to a pharmaceutical form or a food form.

The content of a cellulose acetate having a total degree of acetyl substitution from 0.4 to 1.1 in the food product according to an embodiment of the present disclosure is not particularly limited, but is preferably 0.1 wt. % or above in a food product. This is because, by consuming the food product with such content in one day, an effective amount of cellulose acetate can be ingested. From the perspective of sufficiently increasing IgA in the intestinal tract and maintaining the increased amount of IgA for an extended period of time (for example, from 2 to 4 weeks, or 4 weeks and above) without compromising the taste and texture of food, the content of a cellulose acetate having an total degree of acetyl substitution of from 0.4 to 1.1 is preferably from 0.1 wt. % to less than 5 wt. %, more preferably from 1.5 wt. % to less than 3 wt. %.

Specific examples of target diseases, of which prevention and/or treatment (reduction or prevention of adverse effects) is useful when an intestinal immune-enhancing agent according to an embodiment of the present disclosure is contained in a food product or medicament, include infections caused by pathogenic bacteria belonging to the phylum Proteobacteria, such as *Salmonella* infection, cholera, and *Vibrio parahaemolyticus*. The increase of IgA-producing plasma cells in the intestinal tract, particularly in the lamina propria of the large intestine, is expected to have effects such as increasing IgA, enhancing mucosal immune function, and preventing infections or allergies.

The intake or administration dose of the intestinal immune-enhancing agent according to an embodiment of the present disclosure may be an amount sufficient to bring about the desired intestinal immune-enhancing effect. Specifically, it can be determined empirically in consideration of: the conditions of the administered individual, such as the individual's age, weight, gender, health conditions, and the state of the stomach, small intestine, and large intestine; the ingestion or administration method; the formulation form, etc. The intake or administration dose per serving may be, for example, from 5 mg/kg body weight to 60 mg/kg body weight, or may be from 10 mg/kg body weight to 40 mg/kg body weight. Moreover, the number of times of ingestion by or administration to an individual may be once or more than once; when more than once, the administration may be on a regular basis, on an irregular basis, or as needed. The appropriate number of times can be determined empirically in consideration of the conditions of the administered individual, the ingestion or administration method; the formulation form, etc., as with the intake or administration dose.

Example(s)

Hereinafter, the present invention will be described specifically with reference to examples, but the technical scope of the present invention is not limited by these examples.

Preparation of Cellulose Acetate

One part by weight of cellulose acetate (trade name "L-70", available from Daicel Corporation, having a total degree of acetyl substitution of 2.43 and a viscosity at 6% of 145 mPa.$) was combined with 4.4 parts by weight of acetic acid and 1.9 parts by weight of water, and the mixture was stirred for 3 hours to dissolve the cellulose acetate. The solution was combined with a mixture of 0.58 parts of acetic acid and 0.13 parts by weight of sulfuric acid, and the resulting solution was held at 70° C. to perform hydrolysis. During hydrolysis, water was added to the system in two batches to prevent the precipitation of the cellulose acetate. That is, 0.65 parts by weight of water was added to the system 1 hour after the reaction was started for 5 minutes. Then, after 2 hours, 1.29 parts by weight of water was added to the system for 10 minutes and allowed to react for another 4 hours. The hydrolysis was performed for 7 hours in total. Note that the process from the start of the reaction to the first water addition is referred to as the "first hydrolysis step" (first ripening step), the process from the first water addition to the second water addition is referred to as the "second hydrolysis step" (second aging step), and the process from the second water addition to the end of the reaction is referred to as the "third hydrolysis step" (third ripening step).

After hydrolysis was performed, a 24% magnesium acetate aqueous solution containing 1.1 equivalents of magnesium acetate relative to the sulfuric acid was added to the reaction mixture to stop the reaction. The reaction mixture was added dropwise to an acetone 3.6 times the weight of the reaction mixture over 60 minutes under stirring to form a precipitate. The precipitate was collected as a wet cake having a solid content of 15 wt. % by filtration. 16 parts by weight of acetone/water mixed solvent (having an acetone concentration of 20 wt. %) was added to 1 part by weight of the solid content of the obtained precipitate; after stirring for 8 hours at 40° C., the solid content was collected as a wet cake having a solid content of 15 wt. % by filtration. 16 parts by weight of methanol was added to 1 part by weight of the solid content of the obtained wet cake; after stirring for 1 hour at 25° C., the solid content was collected as a wet cake having a solid content of 15 wt. % by filtration. After repeating this procedure five times, drying was performed to obtain a cellulose acetate having a low degree of substitution.

The total degree of acetyl substitution, the weight average degree of polymerization (DPw), the dispersity (polydispersity Mw/Mn), the measured value of half width of compositional distribution, and the compositional distribution index (CDI) of the obtained cellulose acetate were measured by the methods described above. As a result, the obtained cellulose acetate has a total degree of acetyl substitution of 0.78, a weight average degree of polymerization (DPw) of 124, a dispersity (polydispersity, Mw/Mn) of 2.0, a measured value of half width of compositional distribution of 0.305, and a compositional distribution index (CDI) of 1.90.

Evaluation of Intestinal Immune-Enhancing Agent

Preparation of Feed

Purified feed AIN-93G (REEVE et al. Journal of Nutrition, 123, 1939-1951 (1993)), as well as AIN-93G containing 5 wt. % of cellulose but 2 wt. % of the cellulose is replaced with the cellulose acetate obtained above (hereinafter also referred to as AIN-93G-acetate) were used.

Housing Experiment
Laboratory Animals
Wild-Type Mice

Seven-week-old C57BL/6J male mice were used.
Monocolonized Mice

Male germ-free C57BL/6N mice were housed in an isolator and fed with the K-12 strain (*E. coli*) of *E. coli* (*Escherichia coli*) to create *E. coli* monocolonized mice. Also, *Bacteroides* thetaiotaomicron monocolonized mice were created in the same manner.

AID KO Mice

AID KO mice (that is, Activation-induced cytidine deaminase deficient (knockout) mice) were created in accordance with the method described by Muramatsu et al. (Cell, 102, 553-563 (2000)). Note that AID KO mice do not produce IgA.

Housing Method

Mice used in the experiments described below were housed in the following manner. Eight mice were fed with AIN-93G for 1 week. The feed was freely available. Mice were then grouped into two groups of four individuals each and housed for another 4 weeks. During this 4-week housing, one group was given AIN-93G, which was designated as the Control group. The other group was given AIN-93G-acetate, which was designated as the Acetate group. However, AID KO mice and *E. coli* monocolonized mice were housed with a different number of individuals, namely, 10 individual mice were grouped into two groups of five individuals each.

Fecal IgA Quantification

Feces at day 0, week 1, week 2, week 3, and week 4 from the start of administration of AIN-93G or AIN-93G-acetate were collected, and IgA concentrations in the feces (μg/mL) were quantified. Quantification was performed using a mouse IgA ELISA quantification set (Mouse IgA ELISA Quantification Set, available from Bethyl Laboratories Inc., USA). The results are shown in Table 1.

From the first week after the start of administration of AIN-93G or AIN-93G-acetate, the Acetate group showed a higher IgA concentration than the Control group; and at week 2, the IgA concentration of the Acetate group reached a plateau, and a significant increase in IgA concentrations was observed until week 4.

Quantification of IgA-Coated Bacteria

Microbiota in the feces of wild-type mice housed for four weeks from the start of administration of AIN-93G or AIN-93G-acetate was stained with PE-labeled anti-IgA antibody (Rat anti-mouse IgA, clone 11-44-2, available from SouthernBiotech) and 4,6-diamino-2-phenylindole (DAPI) and analyzed by flow cytometry to obtain the primary data of flow cytometry. Then, DAPI positive cells stained with DAPI were gated on, of which the IgA positive portions were quantified as IgA-coated bacteria. Flow cytometry was performed using FACS Aria II and the data was analyzed by the software FlowJo (available from Tree Star Inc.). The results are shown in FIG. 2. FIG. 2A shows the primary data of flow cytometry, and FIG. 2B shows the percentage (%) of IgA-coated bacteria in DAPI positive cells (% DAPI positive cells).

The Acetate group showed a higher value of the percentage (%) of IgA-coated bacteria in DAPI positive cells (% DAPI positive cells) compared to the Control group. In other words, IgA-coated bacteria increased as a result of increased IgA with affinity for more bacteria in the Acetate group. The ingestion of cellulose acetate according to an embodiment of the present disclosure is expected to have an immune-enhancing effect, such as protecting the intestinal tract from specific bacteria.

Analysis of Microbiota of IgA-Coated Bacteria in Feces

Supernatants were obtained by suspending and centrifuging the feces of wild-type mice housed for four weeks from the start of administration of AIN-93G or AIN-93G-acetate with microbiota phosphate buffered saline (PBS). The bacteria contained in the supernatants were stained with IgA-PE antibody (Rat anti-mouse IgA, clone 11-44-2, available from SouthernBiotech) and DAPI; after magnetic cell separation (using products available from Miltenyi Biotec) was performed and IgA negative bacteria were harvested, FACS Aria II was used to harvest IgA positive bacteria. Bacteria were identified by 16S rRNA gene analysis using these samples. Microbiota analysis results of the feces of wild-type mice in the Acetate group housed for 4 weeks are shown in Table 1, and microbiota analysis results of the feces of wild-type mice in the Control group housed for 4 weeks are shown in Table 2.

TABLE 1

Microbiota analysis results of the feces of wild-type mice in the Acetate group housed for 4 weeks
(Fecal microbiota at phylum level of mice fed with Acetate diet for 4 weeks.)

| | Taxonomy | Microbiota composition (%) | | IgA affinity |
|---|---|---|---|---|
| No. | Phylum | IgA negative | IgA positive | (IgA affinity) |
| 1 | Actinobacteria | 0.4 | 0.5 | |
| 2 | Bacteroidetes | 60.1 | 34.5 | |
| 3 | Firmicutes | 38.4 | 49.6 | |
| 4 | Proteobacteria | 0.7 | 14.8* | + |
| 5 | Tenericutes | 0.1 | 0.0 | |
| 6 | Verrucomicrobia | 0.4 | 0.6 | |
| — | Total | 100.0 | 100.0 | |

*Significantly different in a row (Mann-Whitney U test, p < 0.05).

As shown in Table 1, in the feces of wild-type mice in the Acetate group housed for 4 weeks, bacteria of the phylum Proteobacteria show significant IgA positivity and higher IgA affinity than bacteria of other phyla, including Actinobacteria, Bacteroidetes, Firmicutes, Tenericutes, and Verrucomicrobia. Note that the phylum Proteobacteria includes bacteria that can be pathogenic, such as *Escherichia coli*, *Salmonella*, *Vibrio*, and *Helicobacter*.

TABLE 2

Microbiota analysis results of the feces of wild-type mice in the Control group housed for 4 weeks
(Fecal microbiota at phylum level of mice fed with Control diet for 4 weeks.)

| | Taxonomy | Microbiota composition (%) | | IgA affinity |
|---|---|---|---|---|
| No. | Phylum | IgA negative | IgA positive | (IgA affinity) |
| 1 | Actinobacteria | 0.3 | 1.7* | + |
| 2 | Bacteroidetes | 30.9 | 69.9** | + |
| 3 | Firmicutes | 68.6 | 27.9* | − |
| 4 | Proteobacteria | 0.0 | 0.4 | |
| 5 | Tenericutes | 0.2 | 0.0 | |
| 6 | Verrucomicrobia | 0.0 | 0.1 | |
| — | Total | 100.0 | 100.0 | |

*Significantly different in a row (Mann-Whitney U test, p < 0.05).

As shown in Table 2, in the feces of wild-type mice in the Control group housed for 4 weeks, bacteria of the phylum Proteobacteria do not show IgA positivity and do not have high IgA affinity compared to bacteria of other phyla, including Actinobacteria, Bacteroidetes, Firmicutes, Tenericutes, and Verrucomicrobia.

Quantification of IgA Concentration at Different Sites in Intestinal Tract

In order to examine at which sites in the intestinal tract have the IgA concentration increased, IgA concentrations were quantified separately for each site. The quantification method is described as follows.

Figures 3A, 3B:
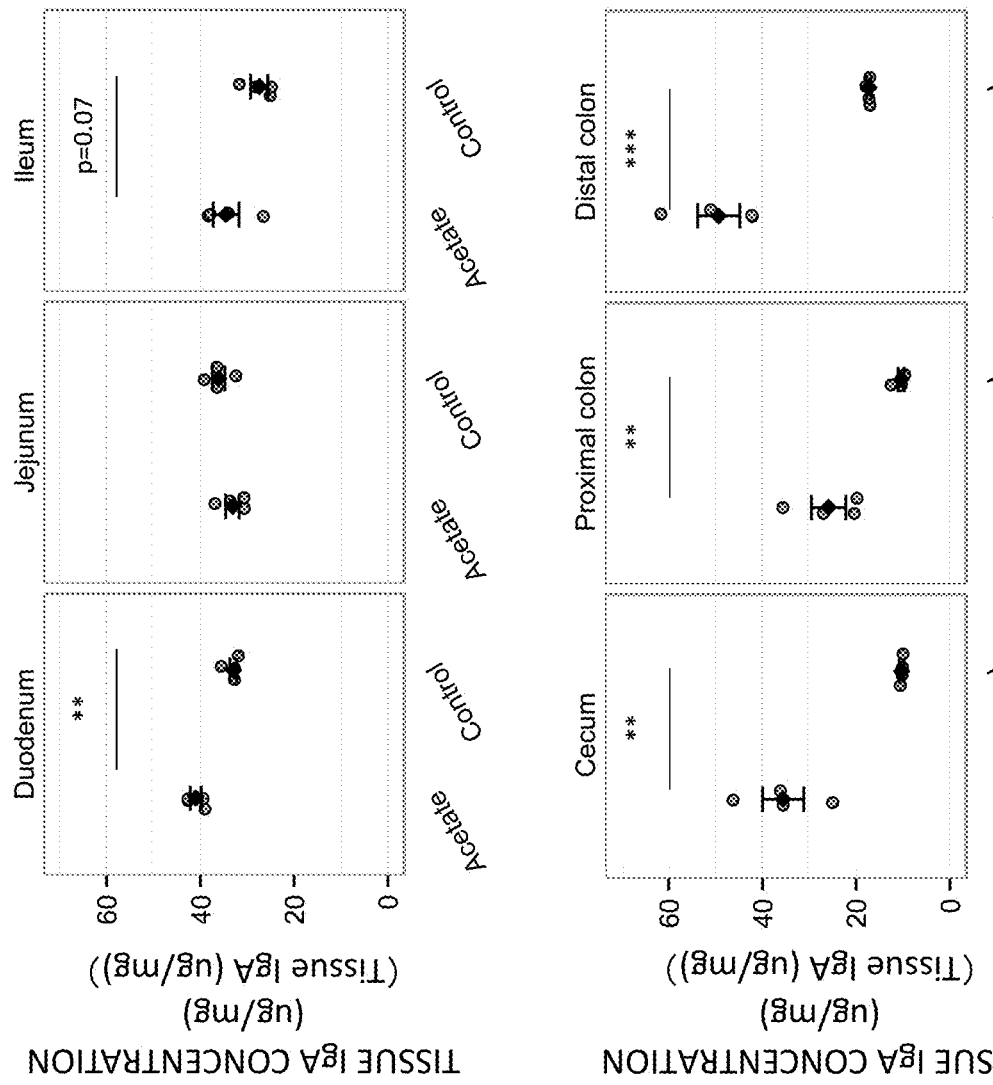
FIGS. 3A and 3B show the IgA quantification results at different sites in the intestinal tract of wild-type mice housed for four weeks.

Tissues from the duodenum, jejunum, ileum, cecum, proximal colon, and distal colon of wild-type mice housed for four weeks from the start of administration of AIN-93G or AIN-93G-acetate were harvested, combined with complete EDTA Free Protease Inhibitor Cocktail Tablet (available from Roche), stored in PBS, and then crushed with stainless beads. Protein concentration was measured by BCA protein assay (using products available from Thermo Fisher Scientific); after unifying the concentration of each tissue, the IgA concentration was quantified. Quantification was performed using a mouse IgA ELISA quantification set (Mouse IgA ELISA Quantification Set, available from Bethyl Laboratories Inc., USA). The results are shown in FIGS. 3A and 3B.

In the duodenum, cecum, proximal colon, and distal colon, the tissue IgA concentration of the Acetate group showed a higher value than that of the Control group. In particular, a large increase was observed from the cecum to the colon.

Quantification of IgA-Producing Plasma Cells in Lamina Propria of Large Intestine In order to isolate lymphocytes from the lamina propria of the large intestine of wild-type mice housed for four weeks from the start of administration of AIN-93G or AIN-93G-acetate, the large intestine was harvested and cleaved in the longitudinal direction, and the feces inside were washed and removed. The washed large intestine was then shaken at 37° C. for 30 minutes in HBSS containing 20 mM EDTA. After removing epithelial cells and adipose tissue, the intestinal tissue was sliced into small pieces, combined with RPMI 1640 medium (containing 2% fetal bovine serum (FBS), 400 units/ml (available from Roche Diagnostics Co., Ltd.); collagenase D, 0.25 units/ml dispase (available from Corning); and 0.1 mg/ml DNaseI (available from Wako Pure Chemical Industries, Ltd.), and shaken for 30 hours in a water bath at 37° C. The digested tissue was washed with RPMI 1640 medium (containing 2% fetal bovine serum (FBS)), resuspended in 10 ml of 35% Percoll (available from GE Healthcare), and layered over 2.5 ml of 70% Percoll in 15 ml of Falcon tubes. Then, the mixture was centrifuged at 2000 rpm for 20 minutes at room temperature, and the cells were separated by a Percoll density gradient. The interface cells were harvested and used as lamina propria lymphocytes.

The isolated lamina propria lymphocytes were suspended in a staining buffer (PBS, 2% FBS) and stained with IgA-PE antibody (Clone: 11-44-1, available from SouthernBiotech) and B220-APC antibody (Clone: RA3-6B2, available from BioLegend).

The lamina propria lymphocytes thus treated were analyzed by flow cytometry. Those gated and stained with the IgA-PE antibody but not stained with the B220-APC antibody were quantified as IgA-producing plasma cells (IgA+ Plasma cells). Also, those stained with both the IgA-PE antibody and the B220-APC antibody were quantified as B cells (IgA+ B cells).

Here, B cells are a type of lymphocyte, and as they mature and differentiate, they become plasma cells specialized in antibody production. Since one B cell can produce only one type of antibody, a B cell will become activated and start producing antibodies only when a matching antigen or bacterial antigen appears.

Flow cytometry was performed using FACScant II, and the data was analyzed with the software FlowJo (available from Tree Star Inc.). The results are shown in FIG. 4. FIG.

Figure 4B:
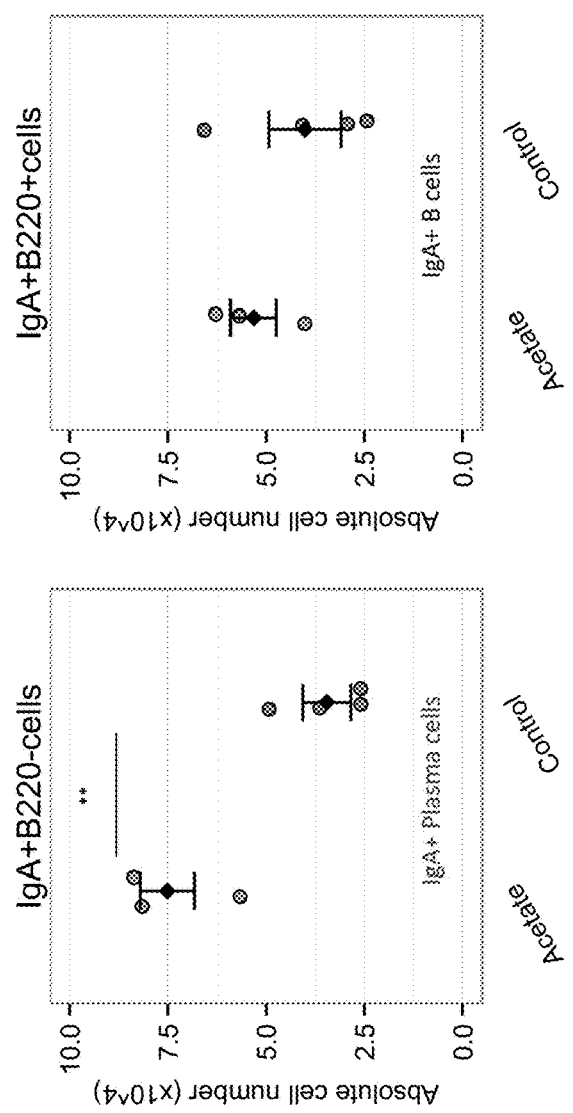
FIGS. 4A and 4B show the quantification results of IgA-producing plasma cells in the lamina propria of the large intestine of wild-type mice housed for four weeks. Specifically.
Figure 4A:
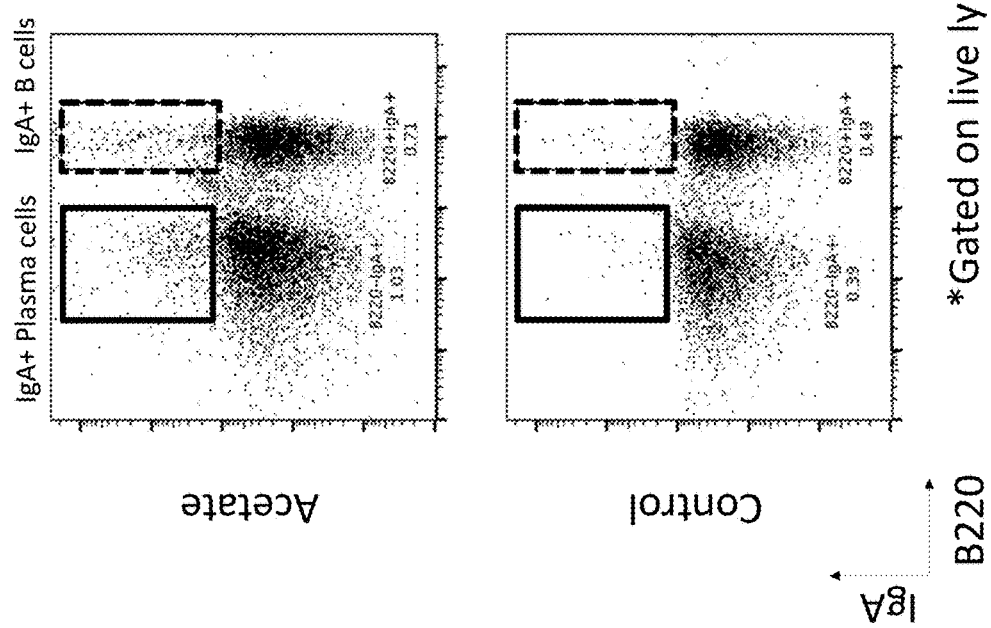

4A shows the primary data of flow cytometry, FIG. 4B shows the number of bacteria (absolute cell number) (×10⁴).

The number of IgA-producing plasma cells in the lamina propria of the large intestine in the Acetate group was significantly increased as compared to the Control group. Thus, an increase in IgA is expected by consuming the cellulose acetate according to an embodiment of the present disclosure.

Quantification of IgA-Coated Bacteria in Cecal Contents and Feces

Microbiota in the cecal contents and feces of *Bacteroides* thetaiotaomicron monocolonized mice and *E. coli* monocolonized mice housed for four weeks from the start of administration of AIN-93G or AIN-93G-acetate are stained with PE-labeled anti-IgA antibody (Rat anti-mouse IgA, clone 11-44-2, available from SouthernBiotech) and 4,6-diamino-2-phenylindole (DAPI) and analyzed by flow cytometry to obtain the primary data of flow cytometry. Then, DAPI positive cells stained with DAPI were gated on, of which the IgA positive portions were quantified as IgA-coated bacteria. Flow cytometry was performed using FACS Aria II and the data was analyzed with the software FlowJo (available from Tree Star Inc.).

Figure 5A:
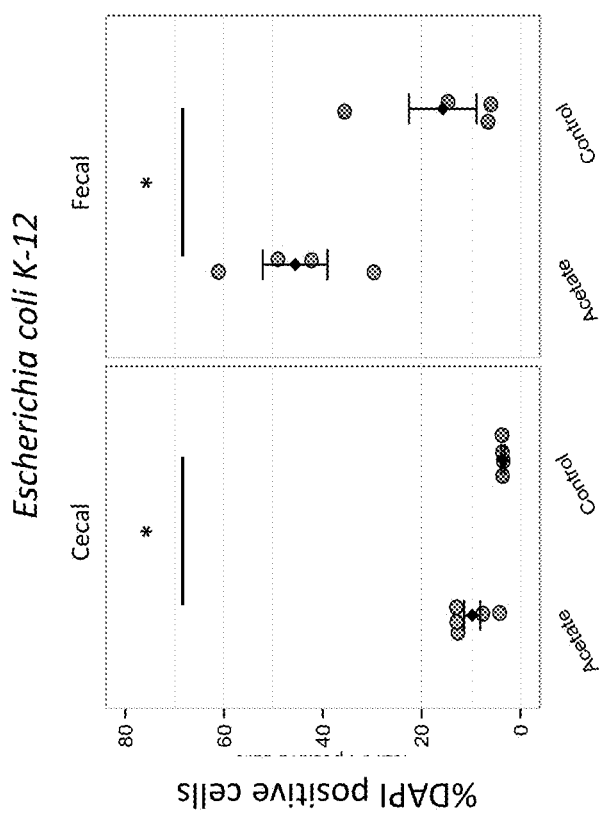
FIGS. 5A and 5B show the quantification results of IgA-coated bacteria in the cecum and feces of monocolonized mice housed for four weeks. Specifically.
Figure 5B:
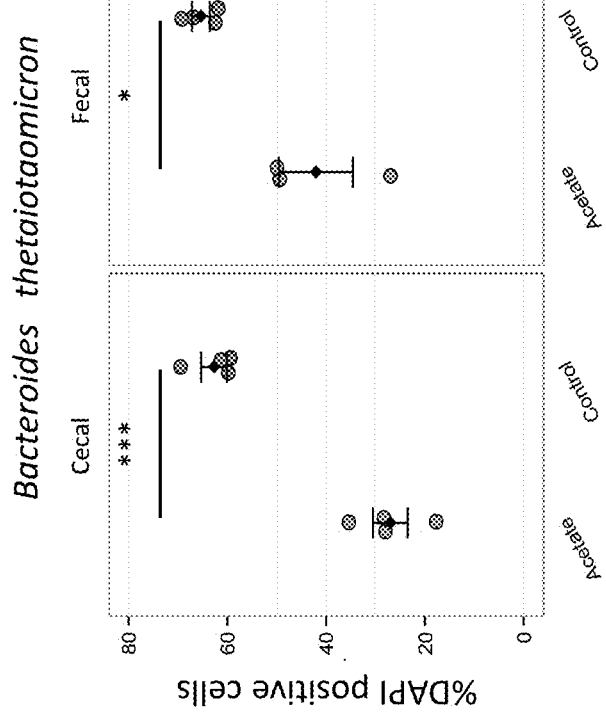

The results are shown in FIG. 5. FIG. 5A shows the percentage (%) of the number of IgA-coated bacteria in the DAPI positive cells (% DAPI positive cells) of the cecum (left: Cecal) and feces (right: Fecal) of *Bacteroides thetaiotaomicron* monocolonized mice. FIG. 5B shows the percentage (%) of the number of IgA-coated bacteria in the DAPI positive cells (% DAPI positive cells) of the cecum (left: Cecal) and feces (right: Fecal) of *E. coli* monocolonized mice, *E. coli* being a type of bacteria of the phylum Proteobacteria.

As shown in FIG. 5A, the percentage of IgA-coated bacteria in the cecum and feces of *Bacteroides* thetaiotaomicron monocolonized mice in the Acetate group was reduced as compared to that of the Control group; however, as shown in FIG. 5B, the percentage of IgA-coated bacteria in the cecum and feces of *E. coli* monocolonized mice in the Acetate group was increased as compared to that of the Control group. In other words, IgA in the Acetate group has increased affinity for the K-12 strain of *Escherichia coli* that belongs to the phylum Proteobacteria. As previously described, the phylum Proteobacteria includes bacteria that can be pathogenic, such as *Escherichia coli*, *Salmonella*, *Vibrio*, and *Helicobacter*; thus, it is expected that the intestinal tract is protected from these bacteria by the IgA induced by the cellulose acetate according to an embodiment of the present disclosure (intestinal protection).

Evaluation of Microbiota in Intestinal Lumen Contents and in Intestinal Mucus Layer Microbiota Analysis Microbiota in the colonic lumen contents and colonic mucus layer of wild-type mice housed for four weeks from the start of administration of AIN-93G or AIN-93G-acetate and AID KO mice housed for four weeks from the start of administration of AIN-93G or AIN-93G-acetate were collected using the method described by Gong et al. (FEMS Microbiol Ecol. 2007 January; 59(1): 147-57), and bacteria were identified by 16S rRNA gene analysis.

Table 3 shows the results of microbiota analysis of the colonic lumen contents and colonic mucus layer of wild-type mice in the Acetate group housed for 4 weeks, and Table 4 shows the results of microbiota analysis of the luminal contents and mucus layer of wild-type mice in the Control group housed for 4 weeks. Furthermore, Table 5 shows the results of microbiota analysis of the luminal contents and colonic mucus layer of AID KO mice in the Acetate group housed for 4 weeks, and Table 6 shows the results of microbiota analysis of the luminal contents and colonic mucus layer of AID KO mice in the Acetate group housed for 4 weeks.

TABLE 3

Results of microbiota analysis of the luminal contents and colonic mucus layer of wild-type mice in the Acetate group housed for 4 weeks (Lumical and mucosal microbiota at phylum level of mice fed with Acetate diet for 4 weeks.)

| No. | Taxonomy Phylum | Microbiota composition (%) | |
| --- | --- | --- | --- |
| | | Luminal (Lumen) | Within the colonic mucus layer (Mucosa) |
| 1 | Actinobacteria | 1.2 | 0.2* |
| 2 | Bacteroidetes | 22.1 | 61.9* |
| 3 | Firmicutes | 74.5 | 37.3* |
| 4 | Proteobacteria | 2.1 | 0.7* |
| 5 | Tenericutes | 0.0 | 0.0 |
| — | Total | 100.0 | 100.0 |

*Significantly different in a row (Mann-Whitney U test, $p < 0.05$).

TABLE 4

Results of microbiota analysis of the luminal contents and colonic mucus layer of wild-type mice in the Control group housed for 4 weeks (Lumical and mucosal microbiota at phylum level of mice fed with Acetate diet for 4 weeks.)

| No. | Taxonomy Phylum | Microbiota composition (%) | |
| --- | --- | --- | --- |
| | | Luminal (Lumen) | Within the colonic mucus layer (Mucosa) |
| 1 | Actinobacteria | 9.3 | 4.3* |
| 2 | Bacteroidetes | 3.0 | 10.7* |
| 3 | Firmicutes | 87.6 | 84.8 |
| 4 | Proteobacteria | 0.0 | 0.0 |
| 5 | Tenericutes | 0.1 | 0.1 |
| — | Total | 100.0 | 100.0 |

*Significantly different in a row (Mann-Whitney U test, $p < 0.05$).

As shown in Table 3, the wild-type mice in the Acetate group are less susceptible to colonization of bacteria of the phylum Proteobacteria in the mucous layer compared to in the luminal contents, given that the results for microbiota composition were 0.7% in the mucous layer and 2.1% in the luminal contents. In contrast, as shown in Table 4, it is hard to draw the conclusion that the wild-type mice in the Control group are less susceptible to colonization of bacteria of the phylum Proteobacteria in the mucous layer compared to in the luminal contents, given that the results for microbiota composition were 0.0% in the mucous layer and also 0.0% in the luminal contents.

TABLE 5

Results of microbiota analysis of the luminal contents and colonic mucus layer of AID KO mice in the Acetate group housed for 4 weeks (Luminal and mucosal microbiota at phylum level of AKD KO mice fed with Acetate diet for 4 weeks.)

| No. | Taxonomy Phylum | Microbiota composition (%) | |
| --- | --- | --- | --- |
| | | Luminal (Lumen) | Within the colonic mucus layer (Mucosa) |
| 1 | Actinobacteria | 11.8 | 1.6* |
| 2 | Bacteroidetes | 2.6 | 6.9* |
| 3 | Cyanobacteria | 0.1 | 0.1 |

TABLE 5-continued

Results of microbiota analysis of the luminal contents and colonic mucus layer of AID KO mice in the Acetate group housed for 4 weeks (Luminal and mucosal microbiota at phylum level of AKD KO mice fed with Acetate diet for 4 weeks.)

| | | Microbiota composition (%) | |
|---|---|---|---|
| No. | Taxonomy Phylum | Luminal (Lumen) | Within the colonic mucus layer (Mucosa) |
| 4 | Deferribacteres | 0.0 | 0.4 |
| 5 | Firmicutes | 69.0 | 58.2* |
| 6 | Proteobacteria | 1.8 | 32.3* |
| 7 | TM7 | 0.0 | 0.0 |
| 8 | Tenericutes | 0.4 | 0.2* |
| 9 | Verrucomicrobia | 14.4 | 0.4* |
| — | Total | 100.0 | 100.0 |

*Significantly different in a row (Mann-Whitney U test, p < 0.05).

TABLE 6

Results of microbiota analysis of the luminal contents and colonic mucus layer of AKD KO mice in the Control group housed for 4 weeks (Luminal and mucosal microbiota at phylum level of AKD KO mice fed with Acetate diet for 4 weeks.)

| | | Microbiota composition (%) | |
|---|---|---|---|
| No. | Taxonomy Phylum | Luminal (Lumen) | Within the colonic mucus layer (Mucosa) |
| 1 | Actinobacteria | 6.8 | 1.0* |
| 2 | Bacteroidetes | 5.8 | 17.3* |
| 3 | Cyanobacteria | 0.4 | 0.4 |
| 4 | Deferribacteres | 0.0 | 2.3* |
| 5 | Firmicutes | 23.6 | 53.8 |
| 6 | Proteobacteria | 1.4 | 22.2* |
| 7 | TM7 | 0.0 | 0.0 |
| 8 | Tenericutes | 0.0 | 0.3 |
| 9 | Verrucomicrobia | 61.8 | 2.8 |
| — | Total | 100.0 | 100.0 |

*Significantly different in a row (Mann-Whitney U test, p < 0.05).

As shown in Table 5, the AID KO mice that do not produce IgA, even in the Acetate group, are very susceptible to colonization of bacteria of the phylum Proteobacteria in the mucous layer compared to in the luminal contents, given that the results for microbiota composition were 32.3% in the mucous layer and 1.8% in the luminal contents. In addition, as shown in Table 6, the AID KO mice in the Control group are also very susceptible to colonization of bacteria of the phylum Proteobacteria in the mucous layer compared to in the luminal contents, given that the results for microbiota composition were 22.2% in the mucous layer and 1.4% in the luminal contents. From the above, it is considered that the increase in IgA contributed to intestinal protection by leading to a decrease in Proteobacteria in the colonic mucus layer.

The invention claimed is:

1. A method for increasing and maintaining of IgA in the intestinal tract of a subject in need thereof, comprising
intaking by the subject or administering to the subject a cellulose acetate having a total degree of acetyl substitution from 0.4 to 1.1;
wherein an intake or administration dose per serving is from 5 mg/kg body weight to 60 mg/kg body weight.

2. The method for increasing and maintaining of IgA in the intestinal tract according to claim 1, wherein the cellulose acetate has a compositional distribution index (CDI) of 2.0 or less, the compositional distribution index (CDI) being defined by the equation below:

CDI=(Measured value of half width of compositional distribution/(Theoretical value of half width of compositional distribution)

wherein the measured value of half width of compositional distribution is a half width of compositional distribution determined by high-performance liquid chromatographic analysis of a cellulose acetate propionate obtained by propionylation of all residual hydroxyl groups of a cellulose acetate,
where DS is the total degree of acetyl substitution; and the theoretical value of half width of compositional distribution=2.35482
$\sqrt{3*DPw*(DS/3)*(1-DS/3)}/DPw$ Dpw is a weight average degree of polymerization determined by gel permeation chromatography-light scattering method using a cellulose acetate propionate obtained by propionylation of all residual hydroxyl groups of the cellulose acetate.

3. A method for treating infections caused by pathogenic bacteria belonging to the phylum Proteobacteria in a subject, where the pathogenic bacteria are *Salmonella*, cholera, or *Vibrio parahaemolyticus*,
the method comprising
intaking by the subject or administering to the subject a cellulose acetate having a total degree of acetyl substitution from 0.4 to 1.1;
wherein an intake or administration dose per serving is from 5 mg/kg body weight to 60 mg/kg body weight.

4. The method for treating infections caused by pathogenic bacteria, belonging to the phylum Proteobacteria according to claim 3, wherein the cellulose acetate has a compositional distribution index (CDI) of 2.0 or less, the compositional distribution index (CDI) being defined by the equation below:

CDI=(Measured value of half width of compositional distribution)/(Theoretical value of half width of compositional distribution)

wherein the measured value of half width of compositional distribution is a half width of compositional distribution determined by high-performance liquid chromatographic analysis of a cellulose acetate propionate obtained by propionylation of all residual hydroxyl groups of a cellulose acetate,
where DS is the total degree of acetyl substitution; and the theoretical value of half width of compositional distribution=2.35482
$\sqrt{3*DPw*(DS/3)*(1-DS/3)}/DPw$ Dpw is a weight average degree of polymerization determined by gel permeation chromatography-light scattering method using a cellulose acetate propionate obtained by propionylation of all residual hydroxyl groups of the cellulose acetate.

5. A method for increasing and maintaining of IgA in the intestinal tract of a subject infected with pathogenic bacteria belonging to the phylum Proteobacteria, comprising
intaking by the subject or administering to the subject a water-soluble dietary fiber selected from a cellulose acetate having a total degree of acetyl substitution from 0.4 to 1.1;
wherein an intake or administration dose per serving is from 5 mg/kg body weight to 60 mg/kg body weight.

* * * * *